US010272075B2

(12) United States Patent
Polymeropoulos et al.

(10) Patent No.: US 10,272,075 B2
(45) Date of Patent: *Apr. 30, 2019

(54) METHOD AND COMPOSITION FOR TREATING AN ALPHA ADRENOCEPTOR-MEDIATED CONDITION (71) Applicant: Vanda Pharmaceuticals, Inc., Washington, DC (US)

(72) Inventors: Mihael H. Polymeropoulos, Potomac, MD (US); Paolo Baroldi, Potomac, MD (US); Curt D. Wolfgang, Germantown, MD (US)

(73) Assignee: Vanda Pharmaceuticals Inc., Washington, DC (US)

( * ) Notice: Subject to any disclaimer, the term of this patent is extended or adjusted under 35 U.S.C. 154(b) by 226 days.

This patent is subject to a terminal disclaimer.

(21) Appl. No.: 14/197,318

(22) Filed: Mar. 5, 2014

(65) Prior Publication Data
US 2014/0194459 A1 Jul. 10, 2014

Related U.S. Application Data (63) Continuation of application No. 12/747,911, filed as application No. PCT/US2008/086733 on Dec. 13, 2008, now Pat. No. 8,729,100.

(60) Provisional application No. 61/013,375, filed on Dec. 13, 2007.

(51) Int. Cl.
| A61K 31/454 | (2006.01) |
| A61K 31/473 | (2006.01) |
| A61K 31/145 | (2006.01) |
| A61K 45/06 | (2006.01) |
| A61K 31/445 | (2006.01) |

(52) U.S. Cl.
CPC .......... *A61K 31/454* (2013.01); *A61K 31/145* (2013.01); *A61K 31/445* (2013.01); *A61K 31/473* (2013.01); *A61K 45/06* (2013.01)

(58) Field of Classification Search
None
See application file for complete search history.

(56) References Cited

U.S. PATENT DOCUMENTS

| 4,772,475 A | 9/1988 | Fukui et al. |
| 5,364,866 A | 11/1994 | Strupczewski et al. |
| 5,658,911 A | 8/1997 | Strupczewski et al. |
| 5,968,544 A | 10/1999 | Beiman et al. |
| 6,140,345 A | 10/2000 | Strupczewski et al. |
| 6,312,728 B1 | 11/2001 | Beiman et al. |
| 6,500,454 B1 | 12/2002 | Percel et al. |
| 6,627,223 B2 | 9/2003 | Percel et al. |
| 6,663,888 B2 | 12/2003 | Percel et al. |
| 8,618,134 B2 | 12/2013 | Polymeropoulos et al. |
| 8,729,100 B2 | 5/2014 | Polymeropoulos et al. |
| 9,446,038 B2 | 9/2016 | Polymeropoulos et al. |
| 2003/0091645 A1 | 5/2003 | Ahlheim et al. |
| 2009/0298880 A1 | 12/2009 | Wolfgang et al. |

FOREIGN PATENT DOCUMENTS

| CA | 2605224 A1 | 10/2006 |
| WO | 03020707 A1 | 3/2003 |
| WO | 03054226 A2 | 7/2003 |
| WO | 2004006886 A2 | 1/2004 |
| WO | 2005012254 A1 | 2/2005 |
| WO | 2006039663 A2 | 4/2006 |
| WO | 2006055734 A2 | 5/2006 |
| WO | 2006108519 A1 | 10/2006 |

OTHER PUBLICATIONS

Nash (Clin Cardiol. Nov. 1990;13(11):764-72) (abstract only).*
PROPECIA® Prescribing Information 2004 (available from FDA website as the 2004 Prescribing Information www.accessdata.fda.gov/drugsatfda_docs/label/2004/20788s002,010,011lbl.pdf).*
Quan et al. (American Journal of Physiology—Renal Physiology Published Sep. 1, 2004 vol. 287 No. 3).*
Sainati et al. (The Journal of Clinical Pharmacology vol. 35, Issue 7, pp. 713-720, Jul. 1995 (abstract only).*
Kalkaman et al. (Neuropsychopharmacology 25 (6): 904-14 (2001)).*
Rosel et al. (Psychiatry Res. 111:105-15 (2002)).*
Liolitsa et al. (Journal of Human Hypertension (2001) 15, 335-339 2001).*
Mehta et al., "Coated Pellets Under the Microscope," Jun. 1985, 7 pages, Pharmaceutical Technology.
Lalla et al., "Controlled-Release Isosorbide Dinitrate Pellets. Part I: Design and Evaluation of Controlled-Release Capsule Dosage Form," Dec. 1993, 3 pages, Journal of Pharmaceutical Sciences, vol. 82,No. 12.
Lalla et al., "Controlled-Release Isosorbide Dinitrate Pellets. Part II: In Vivo Studies," Dec. 1993, 3 pages, Journal of Pharmaceutical Sciences, vol. 82,No. 12.
PCT "Notification Concerning Transmittal of Copy of International Preliminary Report on Patentability" for PCT/US2008/086733, dated Jun. 15, 2010, 6 pages.
PCT "Notification of Transmittal of the International Search Report and the Written Opinion of the International Searching Authority, or the Declaration," for PCT/US2008/086733, dated Feb. 9, 2009, 13 pages.
Hosoda et al., "Blockade of both α1A and α1B-adrenergic receptor asubtype signaling is required to inhibit neointimal formation in the mouse femoral artery," Mar. 2007, pp. H514-H519, Am J Physiol Heart Circ Physiol 293.
Subramanian et al., "Receptor profile of P88-8991 and P95-12113, metabolites of the novel antipsychotic iloperidone," Jan. 2002, Progress in Neuro-Psychopharmacology & Biological Psychiatry, pp. 553-560, XP008087896.
Albayrak, European Application No. 08 859 451.0-2123, Office Action Communication, dated Sep. 27, 2011, 4 pages.
Ling, Singapore Patent Application No. 201004139-0, Search Report and Written Opinion, dated Sep. 22, 2011, 18 pages.

(Continued)

Primary Examiner — Jeffrey S Lundgren
Assistant Examiner — William Y Lee
(74) Attorney, Agent, or Firm — Hoffman Warnick LLC (57) ABSTRACT

Methods and compositions for the treatment of alpha-adrenoceptor mediated conditions.

13 Claims, 4 Drawing Sheets

(56) References Cited

OTHER PUBLICATIONS

Lee, Office Action Communication for U.S. Appl. No. 12/747,911 dated Aug. 12, 2013, 14 pages.
Lee, Notice of Allowance and Fee(s) Due for U.S. Appl. No. 12/747,911 dated Jan. 7, 2014, 6 pages.
Lee, Office Action Communication for U.S. Appl. No. 12/747,911 dated Feb. 1, 2013, 26 pages.
Markel et al., "Increased Platelet Adhesion and Aggregation in Hypertensive Patients: Effect of Atenolol," Br. J. clin. Pharmac. 16:663-8 (1983).
Office Action for U.S. Appl. No. 14/088,877, dated Aug. 6, 2015, (18 pages).
Kalkman et al., "Extended radioligand binding profile of iloperidone: a broad spectrum dopamine/serotonin/norepinephrine receptor antagonist for the management of psychotic disorders," Neuropsychopharmacology. 25 (6):904-14 (2001).
Rosel et al., "Different distributions of the 5-HT reuptake complex and the postsynaptic 5-HT2A receptors in Brodmann areas and brain hemispheres," Psychiatry Res. 111:105-15 (2002).

* cited by examiner

Figure 1. Concentration-Response Curves to Phenylephrine in the Absence and Presence of Test Substance

Figure 2. Concentration-Response Curves to Norepinephrine in the Absence and Presence of Test Substance

METHOD AND COMPOSITION FOR TREATING AN ALPHA ADRENOCEPTOR-MEDIATED CONDITION

CROSS-REFERENCE TO RELATED APPLICATIONS

This application is a continuation of co-pending U.S. application Ser. No. 12/747,911, filed Jun. 12, 2010, which claims priority to PCT/US2008/086733, filed Dec. 13, 2008, which claimed priority to U.S. Provisional Patent Application Ser. No. 61/013,375, filed Dec. 13, 2007, which are hereby incorporated herein.

BACKGROUND OF THE INVENTION

1. Technical Field

This invention relates generally to the treatment of alpha-1 adrenoceptor-mediated conditions.

2. Background

Alpha adrenoceptor-, and more specifically, alpha-1 adrenoceptor-mediated conditions take a variety of forms, and are suffered by a substantial subset of the population. Adrenoceptors (or adrenergic receptors) are a class of G protein-coupled receptors that are targeted by catecholamines. They specifically bind, and are thus activated by, their endogenous ligands, adrenaline (epinephrine) and noradrenaline (norepinephrine). Alpha adrenoceptors bind norepinephrine with a higher affinity than epinephrine. Alpha-1 adrenoceptors are found in smooth muscle tissue, and mediate conditions including hypertension, congestive heart failure, cardiac hyperplasia, urethral obstruction, hyperinsulinemia, lipid disorders, ergot alkaloid poisoning, pheochromocytoma, Raynaud's disease, and male impotency. Some of the known antagonists of alpha-1 adrenoceptors include phenoxybenzamine, phentolamine, prazosin, tamsulosin, and terazosin.

Benign prostatic hyperplasia (also referred to as benign prostatic hypertrophy, or BPH) is a particularly common alpha-1 adrenoceptor-mediated condition. It describes an enlargement of the prostate gland that frequently occurs as men age. The prostate gland comprises two lobes enclosed by an outer layer of tissue, and is located in front of the rectum and just below the bladder, surrounding the urethra. Its primary function is the release of fluid during sexual climax, assisting in the conduction of sperm through the urethra, and helping to neutralize pH of the vaginal canal. (National Kidney and Urologic Diseases Information Clearinghouse (NKUDIC), NIH Publication No. 06-3012: Prostate Enlargement: Benign Prostatic Hyperplasia, at http://kidney.niddk.nih.gov/kudiseases/pubs/prostateenlargement/index.htm#gland (June 2006) (last visited Oct. 26, 2006).)

Because of its proximity and position relative to the bladder and urethra, enlargement of the prostate gland may restrict the flow of urine through the urethra. The layer of tissue surrounding the prostate limits its expansion, causing the gland to press against the urethra, tending to narrow it and clamp it shut. The bladder wall subsequently thickens and becomes irritated, and begins to contract even when it contains only small amounts of urine (thereby causing frequent urination). Eventually, the bladder weakens and loses the ability to empty completely. This may lead to symptoms of a weak or interrupted urinary stream, a feeling of inability to completely empty the bladder, a feeling of delay or hesitation at the start of urination, a need to urinate frequently, especially at night, and a feeling of urgent need to urinate. (Id. at http://kidney.niddk.nih.gov/kudiseases/pubs/prostateenlargement/index.htm#common.)

Drug treatment for BPH focuses on shrinking or preventing further growth or enlargement of the prostate without surgery. Six drugs are commonly prescribed to alleviate clinical symptoms associated with an enlarged prostate, including Finasteride (PROSCAR), dutasteride (AVODART), terazosin (HYTRIN), doxazosin (CARDURA), tamsulosin (FLOMAX), and alfuzosin (UROXATRAL). Finasteride and dutasteride function by inhibiting production of the hormone DHT (dihydrotestosterone). The Medical Therapy of Prostatic Symptoms (MTOPS) Trial, supported by the National Institute of Diabetes and Digestive and Kidney Diseases (NIDDK), recently found that administration of finasteride and doxazosin together is more effective than using either drug alone to relieve symptoms of BPH and prevent further enlargement.

Terazosin, doxazosin, tamsulosin, and alfuzosin, all belonging to the class of drugs known as alpha-blockers, function by relaxing the smooth muscle of the prostate and bladder neck, resulting in improved urine flow and reduced bladder outlet obstruction. (Id. at http://kidney.niddk.nih.gov/kudiseases/pubs/prostateenlargement/index.htm#treatment.) Prazosin (MINIPRESS), an alpha-adrenergic blocker used for treating hypertension, has also been found useful in treating BPH by blocking alpha-1 receptors, which control constriction of the prostate and ureters. (MedlinePlus Drug Information: Prazosin (Systemic) at http://www.nlm.nih.gov/medlineplus/druginfo/uspdi/202475.html (page last updated Oct. 13, 2006) (last visited Oct. 26, 2006).)

SUMMARY OF THE INVENTION

The invention provides methods and compositions for the treatment of benign prostatic hyperplasia (BPH) in a male mammal subject, including a human male, by internally administering to the subject an effective amount of 4-[3-[4-(6-fluoro-1,2,-benzisoxazol-3-yl)-1-piperidinyl]propoxy]-3-methoxy-benzoic acid or a pharmaceutically acceptable salt thereof.

The illustrative aspects of the present invention are designed to solve the problems herein described and other problems not discussed, which are discoverable by a skilled artisan.

BRIEF DESCRIPTION OF THE FIGURES

FIG. 1 shows concentration-response curves to phenylephrine (PE) in the absence and presence of 4-[3-[4-(6-fluoro-1,2,-benzisoxazol-3-yl)-1-piperidinyl]propoxy]-3-methoxy-benzoic acid at four different concentrations: (a) 0.1 uM, (b) 0.3 uM, (c) 1 uM, (d) 3 uM. Square points indicate PE before addition of the test substance and triangular points indicate PE after addition of the test substance.

FIG. 2 shows concentration-response curves to norepinephrine (NE) in the absence and presence of 4-[3-[4-(6-fluoro-1,2,-benzisoxazol-3-yl)-1-piperidinyl]propoxy]-3-methoxy-benzoic acid at four different concentrations: (a) 0.1 uM, (b) 0.3 uM, (c) 1 uM. Square points indicate NE before addition of the test substance and triangular points indicate NE after addition of the test substance.

DETAILED DESCRIPTION

As indicated above, the invention provides methods for the treatment of BPH. Such methods include the administration of an effective amount of 4-[3-[4-(6-fluoro-1,2,-benzisoxazol-3-yl)-1-piperidinyl]propoxy]-3-methoxy-benzoic acid or a pharmaceutically acceptable salt thereof, alone or in combination with one or more additional active agents. These additional active agents may comprise one or more additional alpha-adrenoceptor antagonists, one or more steroid-5-alpha reductase inhibitors, or one or more additional alpha adrenoceptor antagonists in combination with one or more steroid-5-alpha reductase inhibitors.

As used herein, "effective amount" means an amount that prevents or delays onset of signs and symptoms of the condition being treated for, or that eliminates or alleviates, i.e., lessens the severity or reduces the frequency of occurrence, of signs and symptoms of the condition. In addition, "treatment," "treating," and "treat" shall mean treatment or prevention, i.e., the treatment or prevention of an alpha-adrenoceptor-mediated condition.

The present invention contemplates use of 4-[3-[4-(6-fluoro-1,2,-benzisoxazol-3-yl)-1-piperidinyl]propoxy]-3-methoxy-benzoic acid or a pharmaceutically acceptable salt thereof, as well as esters, solvates, hydrates, crystalline and amorphous forms, and polymorphs thereof.

4-[3-[4-(6-fluoro-1,2,-benzisoxazol-3-yl)-1-piperidinyl]propoxy]-3-methoxy-benzoic acid is a metabolite of Iloperidone. Iloperidone is disclosed in U.S. Pat. Nos. 5,364,866, 5,658,911, and 6,140,345, each of which is incorporated herein by reference. In some cases, it may be advantageous to use iloperidone or an iloperidone metabolite preferentially in patients with certain genotypes as disclosed, e.g., in International Patent Application Publication Nos. WO2006039663 and WO2003054226, which are also incorporated herein by reference.

4-[3-[4-(6-fluoro-1,2,-benzisoxazol-3-yl)-1-piperidinyl]propoxy]-3-methoxy-benzoic acid has greatest affinity and is most potent for alpha 1 adrenoceptors and the serotonin $5HT_{2A}$ receptor; it has slightly greater affinity/potency for alpha 1 adrenoceptors than for alpha 2 adrenoreceptors and has very weak if any activity with respect to the dopamine, histamine and serotonin receptors (other than $5HT_{2A}$).

4-[3-[4-(6-fluoro-1,2,-benzisoxazol-3-yl)-1-piperidinyl]propoxy]-3-methoxy-benzoic acid appears not to cross the blood-brain barrier. Specifically, in DMPK studies using rats treated with [14C] 4-[3-[4-(6-fluoro-1,2,-benzisoxazol-3-yl)-1-piperidinyl]propoxy]-3-methoxy-benzoic acid, none of the animals had measurable radioactivity concentrations in the brain. Therefore, 4-[3-[4-(6-fluoro-1,2,-benzisoxazol-3-yl)-1-piperidinyl]propoxy]-3-methoxy-benzoic acid is particularly useful in conditions that are not mediated, to a substantial degree, by receptors in the brain.

A method according to the present invention includes administering to an animal suffering from an enlarged prostate, or BPH, an effective amount of 4-[3-[4-(6-fluoro-1,2,-benzisoxazol-3-yl)-1-piperidinyl]propoxy]-3-methoxy-benzoic acid or a pharmaceutically acceptable salt thereof.

4-[3-[4-(6-fluoro-1,2,-benzisoxazol-3-yl)-1-piperidinyl]propoxy]-3-methoxy-benzoic acid and pharmaceutically-acceptable salts thereof may be administered separately from or together with one or more additional alpha adrenoceptor antagonists. In such an embodiment, the one or more additional alpha adrenoceptor antagonist to be administered together with 4-[3-[4-(6-fluoro-1,2,-benzisoxazol-3-yl)-1-piperidinyl]propoxy]-3-methoxy-benzoic acid or a pharmaceutically acceptable salt thereof may be selected from: Doxazosin, e.g., CARDURA; Prazosin, e.g., MINIPRESS; Terazosin, e.g., HYTRIN; Rec 15/2739; and tamsulosin, e.g., FLOMAX. Such an embodiment, for example, comprises a pill or capsule having both active pharmaceutical ingredients either admixed together or having each active pharmaceutical ingredient in a discrete portion of the pill or capsule. Metabolites, prodrugs, polymorphs, hydrates, solvates, and salts of the above compounds that are directly or indirectly active can, of course, also be used in the practice of this invention.

In addition, 4-[3-[4-(6-fluoro-1,2,-benzisoxazol-3-yl)-1-piperidinyl]propoxy]-3-methoxy-benzoic acid or a pharmaceutically-acceptable salt thereof, may be co-administered separately from or together with an effective amount of one or more additional alpha-adrenoceptor antagonists, one or more steroid-5-alpha reductase inhibitors, or one or more additional alpha adrenoceptor antagonists in combination with one or more steroid-5-alpha reductase inhibitors. In this embodiment, the steroid-5-alpha reductase inhibitor may be, for example, finasteride.

Compounds administered according to the invention may take any number of forms, including, for example, tablets, capsules, oral solutions, intravenous solutions, intramuscular injectables, intradermal injectables, suppositories, patches, inhalents, and nasal sprays. Similarly, such compounds may be provided in immediate release formulations, extended release formulations, or long-term injectable formulations (e.g., 28 day depot formulations). In addition, methods according to the invention may include once-, twice-, or thrice-daily administrations.

An effective amount of may be administered to a subject mammal (typically a human but other mammals, e.g., farm animals, pets and racing animals, can also be treated) by a number of routes. An effective amount is an amount that prevents or delays onset of signs and symptoms of enlargement of the prostate or that eliminates or alleviates, i.e., lessens the severity or reduces the frequency of occurrence, of signs and symptoms of prostate enlargement. So, e.g., an effective amount is an amount that prevents, reverses, or slows prostate enlargement or that alleviates the clinical symptoms of an enlarged prostate such as the symptoms recited above.

An effective amount may vary quantitatively depending upon, e.g., the patient, the severity of the disorder or symptom being treated, and the route of administration. Such dose can be determined by routine studies. In general, for systemic administration, e.g., oral administration, an effective amount is likely to be about 1 to about 500 mg/day, e.g., about 5 to about 100 mg/day, or about 0.01 to about 10 mg/kg/day, e.g., about 0.1 to about 5 mg/kg/day or about 0.5 to about 1.5 mg/kg/day.

It will be understood that the dosing protocol will be determined by a physician in the light of the relevant circumstances. These include, for example, the condition to be treated, the chosen route of administration, the age, weight, and response of the individual patient, and the severity of the patient's symptoms. Patients should of course be monitored for possible adverse events.

For therapeutic or prophylactic use, 4-[3-[4-(6-fluoro-1,2,-benzisoxazol-3-yl)-1-piperidinyl]propoxy]-3-methoxy-benzoic acid or pharmaceutically-acceptable salts thereof will normally be administered as a pharmaceutical composition comprising, as the (or an) essential active ingredient, at least one such compound in association with a solid or liquid pharmaceutically acceptable carrier and, optionally, with pharmaceutically acceptable excipients employing standard and conventional techniques.

Pharmaceutical compositions useful in the practice of this invention include suitable dosage forms for oral, parenteral (including subcutaneous, intramuscular, intradermal and intravenous), transdermal, bronchial or nasal administration.

Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. The pharmaceutical compositions may be prepared by conventional techniques appropriate to the desired preparation containing appropriate amounts of iloperidone or an active metabolite thereof. See, for example, REMINGTON'S PHARMACEUTICAL SCIENCES, Mack Publishing Company, Easton, Pa., 17th edition, 1985.

In making pharmaceutical compositions for use in the invention, the active ingredient(s) will usually be mixed with a carrier, or diluted by a carrier, or enclosed within a carrier, which may be in the form of a capsule, sachet, paper, or other container. When the carrier serves as a diluent, it may be a solid, semi-solid, or liquid material which acts as a vehicle, excipient, or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

Some examples of suitable excipients and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate, and mineral oil. The formulations can additionally include lubricating agents, wetting agents, emulsifying and suspending agents, preserving agents, sweetening agents, and/or flavoring agents. The compositions of the invention may be formulated so as to provide quick, sustained, or delayed release of the active ingredient after administration to the patient.

Administration of 4-[3-[4-(6-fluoro-1,2,-benzisoxazol-3-yl)-1-piperidinyl]propoxy]-3-methoxy-benzoic acid or a pharmaceutically-acceptable salt thereof, according to any of the above embodiments, for treating BPH or for other indications, may be accomplished through the use of a controlled release pharmaceutical dosage form, e.g., delayed, sustained, or pulsatile release. By "controlled release" is meant that the absorption of the active pharmaceutical ingredient (API) is delayed, sustained or delayed and sustained relative to an immediate release oral form for administration by swallowing. Such a dosage form is disclosed, e.g., in U.S. Pat. No. 4,772,475, which is incorporated herein by reference.

For example, a controlled release formulation of the invention includes one in which: 4-[3-[4-(6-fluoro-1,2,-benzisoxazol-3-yl)-1-piperidinyl]propoxy]-3-methoxy-benzoic acid or a pharmaceutically-acceptable salt thereof, dissolves at a rate of between about 3% and about 15% per hour, more preferably between about 4% and about 13% per hour, and most preferably between about 5% and about 7% per hour in a standard dissolution assay (e.g., an aqueous solvent at (1) pH 4.5, (2) pH 6.8 or (3) 0.1N HCl, at 37 C), thereby providing a slow, substantially constant dosage of 4-[3-[4-(6-fluoro-1,2,-benzisoxazol-3-yl)-1-piperidinyl]propoxy]-3-methoxy-benzoic acid or a pharmaceutically acceptable salt thereof over a period of between about 16 and about 24 hours. In another embodiment, 4-[3-[4-(6-fluoro-1,2,-benzisoxazol-3-yl)-1-piperidinyl]propoxy]-3-methoxy-benzoic acid or a pharmaceutically acceptable salt thereof is released in a pulsatile profile, e.g., to release approximately 25% of drug shortly following administration and approximately 25% of drug at more or less 2 hours, 4 hours, and 6 hours post-administration, or to release approximately 50% of drug shortly following administration and approximately 25% of drug at more or less 2 hours and 4 hours post-administration or to release approximately 50% of drug shortly following administration and approximately 25% of drug at more or less 4 hours and 6 hours post-administration.

The controlled release dosage forms of the present invention may employ a number of controlled release technologies for oral delivery. For example, Lalla and Bhat describe a method of coating DCP granules with the vasodilator isosorbide dinitrate to slow its release. Such method for preparing a pharmaceutical composition of the present invention in controlled release form comprises first spraying DCP granules with a sugar syrup and sorting the coated granules to select those having diameters between about 500 and about 600 μm. Next, a coating of 4-[3-[4-(6-fluoro-1,2,-benzisoxazol-3-yl)-1-piperidinyl]propoxy]-3-methoxy-benzoic acid or a pharmaceutically-acceptable salt or ester thereof ("active pharmaceutical ingredient" or "API") is sprayed onto the surfaces of the granules and the granules allowed to dry. A layer of an acidic buffering agent can be applied under and/or above the drug layer in order to maintain an acidic microenvironment in within the pellet matrix. Finally, a polymeric coating is applied to the dried API-coated granules. Alternatively, the dried granules may be pressed into a tablet. See, J. K. Lalla & Shruti U. Bhat, Controlled-Release Isosorbide Dinitrate Pellets. Part I: Design and Evaluation of Controlled-Release Capsule Dosage Form, J. Pharm. Sci., 82(12):1288-1291 (1993); J. K. Lalla & Shruti U. Bhat, Controlled-Release Isosorbide Dinitrate Pellets. Part II: In Vivo Studies, J. Pharm. Sci., 82(12): 1292-1295 (1993), both of which are hereby incorporated by reference.

U.S. Pat. No. 5,968,554 to Beiman, et al. teaches a multi-layered controlled release dosage capable of delivering a pharmaceutical to both the stomach and the duodenum. Similarly, U.S. Pat. No. 6,312,728, also to Beiman, et al., teaches a multi-layered controlled release dosage capable of delivering a pharmaceutical to both the duodenum and large intestine or colon or to the stomach, duodenum, and large intestine or colon. Both references are incorporated herein by reference.

A number of related controlled-release dosages and methods have been described by Percel et al. For example, U.S. Pat. No. 6,627,223 describes a pharmaceutical dosage comprised of timed, sustained-release (TSR) beads having at least two coated membrane barriers, the composition and thickness of the barriers determining the lag time and duration of drug release. In one embodiment, a first membrane barrier is an enteric polymer and a second membrane is a mixture of a water-insoluble polymer and an enteric polymer. Such a configuration permits one or more pulses of a therapeutic agent in a plasma concentration-time profile.

U.S. Pat. No. 6,500,454, also to Percel et al., describes a dosage unit for providing a circadian-like release of propranolol to mimic the time-dependent physiological need for the drug. U.S. Pat. No. 6,663,888, also to Percel et al., describes a similar dosage for the circadian-like release of a histamine H2 antagonist. Each of the Percel et al. references above is incorporated herein by reference.

Other controlled-release methods known in the art are within the scope of the present invention, including, for example, conventional pan coating, perforated pan coating, fluidized-bed coating, top-spray coating, bottom-spray coating, and tangential-spray coating. See, e.g., Atul M. Mehta & David M. Jones, Coated Pellets Under the Microscope, Pharm. Tech., June 1985, which is also hereby incorporated by reference. Various excipients may be incorporated into the controlled-release dosage form of the invention. Such excipients include, for example, Eudragit® polymers (Rohm & Haas), ethylcellulose, Ethocel® polymers (Dow Chemical Company), triethyl citrate, hydroxypropyl methylcellulose (HPMC), polyvinylpyrrolidone (PVP), sugars, and acidic buffering agents. Generally, such excipients would comprise the bulk of a controlled-release dosage.

In an alternative illustrative embodiment, a controlled release dosage form of the invention is designed to provide intermittent, or pulsatile, release of drug. In such embodiment, the dosage form may release 2, 3, 4, 5, or even 6 aliquots of drug over a period of several hours, e.g., 2-24 hours, 8-24 hours, or 16-24 hours. An illustrative pulsatile delivery dosage form of the invention releases drug in 3 aliquots, each in a separate "compartment," one that releases drug primarily in the duodenum, a second that releases drug primarily in the jejunum, and a third that releases drug primarily in the ileum. The amount of drug released in each aliquot can be an equal fraction of the total amount or the amounts can be different. In pulsatile release embodiments of this invention, the choice of buffering agent and counterion can differ for the different aliquots, depending, for example, on where in the GI tract a particular aliquot is expected to be released.

Various formulations and methods of administering iloperidone have been described. For example, PCT Publication No. WO 2004/006886 A2 describes an injectable depot formulation comprising iloperidone crystals; microencapsulated depot formulations of iloperidone and a polyglycolide polylactide glucose star polymer are described in U.S. Patent Application Publication No. 20030091645; and methods for the administration of iloperidone directed toward, inter alia, eliminating or minimizing the prolongation of a corrected electrocardiographic QT (QTc) interval associated with increased concentrations of iloperidone or iloperidone derivatives are described in U.S. Provisional Patent Application No. 60/614,798, filed 30 Sep. 2004, all of which are incorporated herein by reference.

In another illustrative embodiment, the invention comprises co-administering 4-[3-[4-(6-fluoro-1,2,-benzisoxazol-3-yl)-1-piperidinyl]propoxy]-3-methoxy-benzoic acid and one or more additional alpha adrenoceptor antagonists, one or more steroid-5-alpha reductase inhibitors, or a combination of one or more additional alpha adrenoceptor antagonists and one or more steroid-5-alpha reductase inhibitors at approximately the same time or at different time intervals, such that an effective amount of each is maintained in the patient's bloodstream in the appropriate amounts at the appropriate times.

In a related embodiment, a kit comprises pharmaceutical dosage units of one agent alone, e.g., 4-[3-[4-(6-fluoro-1,2,-benzisoxazol-3-yl)-1-piperidinyl]propoxy]-3-methoxy-benzoic acid, and other pharmaceutical dosage units comprising a different or both agents. Such a kit could facilitate, e.g., administration of the alpha adrenoceptor antagonist to be taken at different time intervals than the one or more additional alpha adrenoceptor antagonists, one or more steroid-5-alpha reductase inhibitors, or the combination of one or more additional alpha adrenoceptor antagonists and one or more steroid-5-alpha reductase inhibitors.

When used in such combinations, the dose of each agent is expected to be approximately the same as, or less than, an effective amount of either alone. For example, each pharmaceutically active ingredient can be administered in doses that are about 20% to about 80% of the dose in which each ingredient would be administered alone.

The two (or more) agents can be administered more or less simultaneously, i.e., concomitantly (e.g., within about 0 to about 5 minutes of each other, preferably within about a minute apart), or they can be administered at different times. For example, the compositions can be formulated in a unit dosage form, each dosage containing both active ingredients. The term "unit dosage form" refers to physically discrete units suitable as unitary dosages for human subjects and other animals, each unit containing a predetermined quantity of active material calculated to produce the desired prophylactic or therapeutic effect over the course of a treatment period, in association with the required pharmaceutical carrier.

Unit dosage forms of the invention, whether they comprise 4-[3-[4-(6-fluoro-1,2,-benzisoxazol-3-yl)-1-piperidinyl]propoxy]-3-methoxy-benzoic acid or a pharmaceutically-acceptable salt thereof as the sole active pharmaceutical ingredient or in combination with another agent, can also be formulated in a controlled release form, e.g., delayed, sustained, or pulsatile release. With such form, in the case of combinations, 4-[3-[4-(6-fluoro-1,2,-benzisoxazol-3-yl)-1-piperidinyl]propoxy]-3-methoxy-benzoic acid or a pharmaceutically-acceptable salt thereof can be released at the same or different rates and times as the other agent or agents.

In a related aspect, this invention comprises a method of promoting, marketing, or selling a pharmaceutical composition comprising 4-[3-[4-(6-fluoro-1,2,-benzisoxazol-3-yl)-1-piperidinyl]propoxy]-3-methoxy-benzoic acid or a pharmaceutically-acceptable salt thereof that comprises disseminating information to prospective patients, formulary managers, or physicians or other prescribers about the compound, such information including that 4-[3-[4-(6-fluoro-1,2,-benzisoxazol-3-yl)-1-piperidinyl]propoxy]-3-methoxy-benzoic acid or a pharmaceutically-acceptable salt thereof is an alpha1 adrenoceptor antagonist. Such information may also include that the compound has been shown to be useful in the treatment of prostate enlargement, or BPH.

In a related aspect, the invention comprises a system for disseminating such information, such system comprising, for example, a data storage medium wherein such information is stored, a means for retrieving such information from the data storage medium, such as a computer, and a means for disseminating the retrieved information to relevant persons, such as by sending the information electronically or by printing and physically distributing copies of the printed information.

EXAMPLES

The following examples are illustrative and not limiting. All experiments described hereinbelow were conducted under the supervision of Dr. Stefano Palea of UROsphere in Toulouse, France.

Example 1

The purpose of this example was to evaluate the effects of the test substance, i.e., 4-[3-[4-(6-fluoro-1,2,-benzisoxazol-3-yl)-1-piperidinyl]propoxy]-3-methoxy-benzoic acid, on phenylephrine (PE)-induced contraction in the prostatic smooth muscle of male rabbits.

It is well established in the literature that the rabbit is a good model for the pharmacology of the lower urinary tract. In particular, a correlation was found between affinities for cloned alpha1a-adrenoceptors and antagonist potency ($pK_b$) values for several alpha1-adrenoceptors antagonists in the rabbit isolated prostate (Martin et al., J. Pharmacol. Expr. Ther. 282: 228-35, 1997).

Briefly, following animal sacrifice, transverse preparations of the prostate were suspended vertically in 25 mL glass organ baths under a loading tension of 1 g and placed in an oxygenated, modified Krebs solution (NaCl 114 mM, KCl 4.7 mM, $CaCl_2$ 2.5 mM, $KH_2PO_4$ 1.2 mM, $NaHCO_3$ 25 mM, glucose 11.7 mM (pH 7.4, gassed with 95% $O_2$ and 5% $CO_2$ at 37° C.). Propranolol (1 µM), desipramine (0.1 µM), deoxycorticosterone (3 µM) and normetanephrine (1 µM) were added to the Krebs-Henseleit solution in order to block beta-adrenoceptors, neuronal and extraneuronal uptake and catechol-O-methyl transferase, respectively.

After 60 min of equilibration, smooth muscle strips were exposed to 30 µM PE to measure their viability. Strips having low contractile responses (<0.5 g) were discarded. Following a 30 min washout period, a first concentration-response curve (CRC) to PE (in the range 0.1 µM-1 mM) was obtained by cumulative additions as half-log unit concentrations increments. Then, tissues were washed for 60 min and incubated for 60 min with the test substance (at four different concentrations) before a second PE CRC was obtained (in the range 0.1 µM-10 mM). Only one concentration for the test substance was tested on each single smooth muscle strip. In different strips, a single concentration of tamsulosin (0.01 µM) was tested as a reference compound.

In this experiment, the $pK_b$ value for alfuzosin was 7.25, a value similar to the corresponding $pK_b$ value found for the same antagonist on human isolated prostatic adenoma obtained from BPH patients (7.78, Palea et al., Neurourol. Urodyn. 19 (Suppl.): 431-33, 2000).

Mean values of the contractile response to 30 µM PE failed to demonstrate a significant statistical difference (p=0.0678 by Kruskall-Wallis test).

The maximal response (Emax) value of the CRCs to PE following 60 min incubation (with a common solvent for 4-[3-[4-(6-fluoro-1,2,-benzisoxazol-3-yl)-1-piperidinyl]propoxy]-3-methoxy-benzoic acid or tamsulosin) was significantly lower than the corresponding value obtained before incubation (137.7% vs. 166.2%; p=0.005). However, this was not the case in the presence of the test substance at 0.1, 0.3 and 1 µM demonstrating that, in the rest of the experiments, two consecutive CRC to PE on the rabbit prostate were perfectly reproducible.

4-[3-[4-(6-fluoro-1,2,-benzisoxazol-3-yl)-1-piperidinyl]propoxy]-3-methoxy-benzoic acid concentration-dependently antagonized the PE-induced contractions (n=6 for each dose). See, FIG. 1. The –log EC50 (pEC50) values for PE before antagonist incubation were significantly different from pEC50 values obtained in the presence of each 4-[3-[4-(6-fluoro-1,2,-benzisoxazol-3-yl)-1-piperidinyl]propoxy]-3-methoxy-benzoic acid concentration or tamsulosin at 0.01 µM. Emax values were unaffected by the presence of the two antagonists. (EC50 is the concentration required to obtain 50% of a biological effect.)

The antagonist potency ($pA_2$, i.e., "minus one times the concentration of antagonist causing the agonist to double its concentration in order to obtain the same effect) for 4-[3-[4-(6-fluoro-1,2,-benzisoxazol-3-yl)-1-piperidinyl]propoxy]-3-methoxy-benzoic acid, estimated by the Schild plot, was equal to 7.47. The $pA_2$ for tamsulosin, calculated from the dose-ratio of pEC50 values, was equal to 10.21, which is in accordance with a previous report on the rabbit isolated prostate ($pK_b$=9.74; Martin et al., 1997).

Based on the similar pEC50 values for PE in the presence of tamsulosin at 0.01 µM (2.65) and 4-[3-[4-(6-fluoro-1,2,-benzisoxazol-3-yl)-1-piperidinyl]propoxy]-3-methoxy-benzoic acid at 3 µM (2.35), it is estimated that, on this rabbit preparation, tamsulosin is 300 times more potent than 4-[3-[4-(6-fluoro-1,2,-benzisoxazol-3-yl)-1-piperidinyl]propoxy]-3-methoxy-benzoic acid.

These results showed that 4-[3-[4-(6-fluoro-1,2,-benzisoxazol-3-yl)-1-piperidinyl]propoxy]-3-methoxy-benzoic acid is a functional antagonist of the alpha1-adrenoceptors activated by PE on the rabbit isolated prostatic smooth muscle. Its potency ($pA_2$=7.47) is approximately equal (Martin et al., 1997) to the potencies shown by alpha1-adrenoceptor antagonists on the market for the treatment of BPH, e.g. alfuzosin, doxazosin and terazosin.

Example 2

The purpose of this experiment was to evaluate the effects of 4-[3-[4-(6-fluoro-1,2,-benzisoxazol-3-yl)-1-piperidinyl]propoxy]-3-methoxy-benzoic acid on norepinephrine (NE)-induced contraction in the prostatic adenoma obtained from patients affected by benign prostatic hyperplasia (BPH).

The experimental protocol used in this example is similar to the one described in a previous paper to measure the antagonistic potency of tamsulosin (Noble et al., Br. J. Pharmacol. 120: 231-38, 1997).

Briefly, human prostatic adenoma was obtained from 6 patients (mean age 71±5 years) undergoing transvesical adenomectomy of the prostate because of BPH. Prostatic strips were mounted in glass organ baths containing a modified Krebs-Henseleit solution (NaCl 114 mM, KCl 4.7 mM, $CaCl_2$ 2.5 mM, $KH_2PO_4$ 1.2 mM, $NaHCO_3$ 25 mM, glucose 11.7 mM, ascorbic acid 1.1 mM (pH 7.4, gassed with 95% $O_2$ and 5% $CO_2$ at 37° C.) under 1.5 g tension. After 60 min of equilibration, the strips were exposed to 30 µM NE to measure their viability. Strips having a contractile response <0.3 g were discarded.

After washout and 60 min of re-equilibration to re-establish baseline tension, a first cumulative concentration-response curve to NE (in the range 0.1 µM-1 mM) was constructed until a plateau of contraction was reached. After 60 min washout to re-establish baseline tension, the test substance, 4-[3-[4-(6-fluoro-1,2,-benzisoxazol-3-yl)-1-piperidinyl]propoxy]-3-methoxy-benzoic acid, at 0.1, 0.3 and 1 µM or the reference substance (tamsulosin) at 0.01 µM for the two substances were incubated for 60 min, then a second CRC to NE was constructed. Only one concentration of antagonist was tested in a single strip. Controls were obtained incubating strips for 60 min with the common solvent (DMSO) for 4-[3-[4-(6-fluoro-1,2,-benzisoxazol-3-yl)-1-piperidinyl]propoxy]-3-methoxy-benzoic acid and tamsulosin. The quantity of DMSO in the organ baths was equal to 0.1%.

Mean values of the contractile response to 30 μM NE failed to demonstrate a statistically significant difference (p>0.05 by ANOVA one-way).

The pEC50 value of the second CRC to NE was significantly lower (4.72+/−0.088) than the corresponding value obtained in the first CRC (5.17+/−0.088; p<0.001).

Figure 1A:
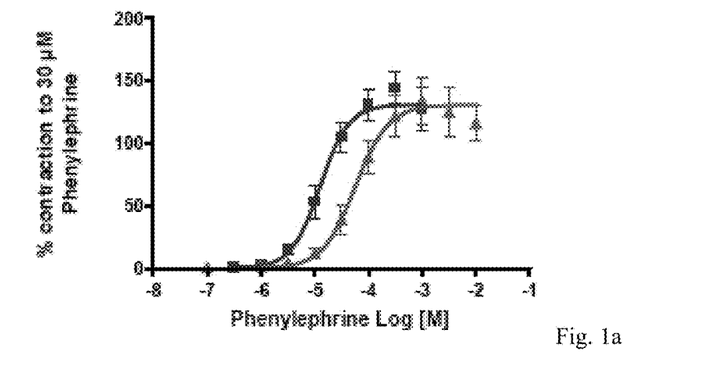
Figure 1B:
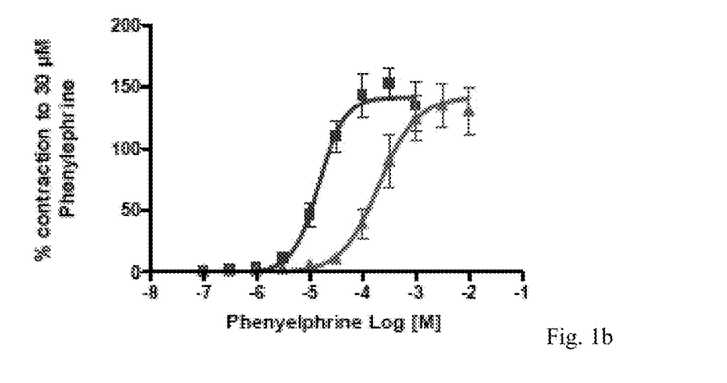
Figure 1C:
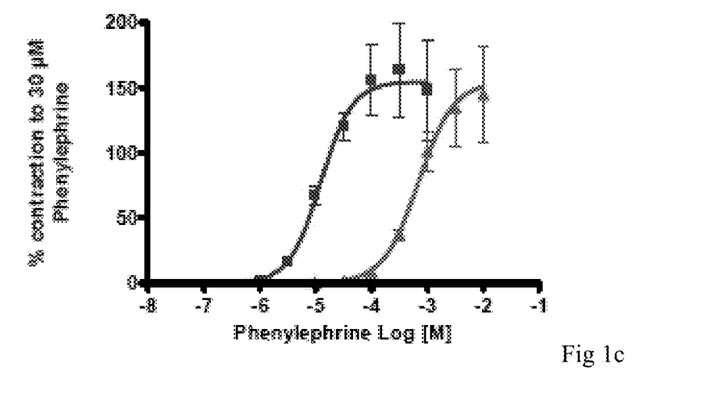
Figure 1D:
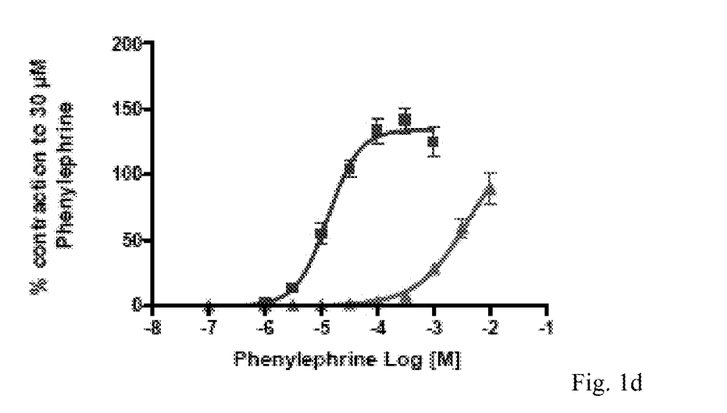
Figure 2A:
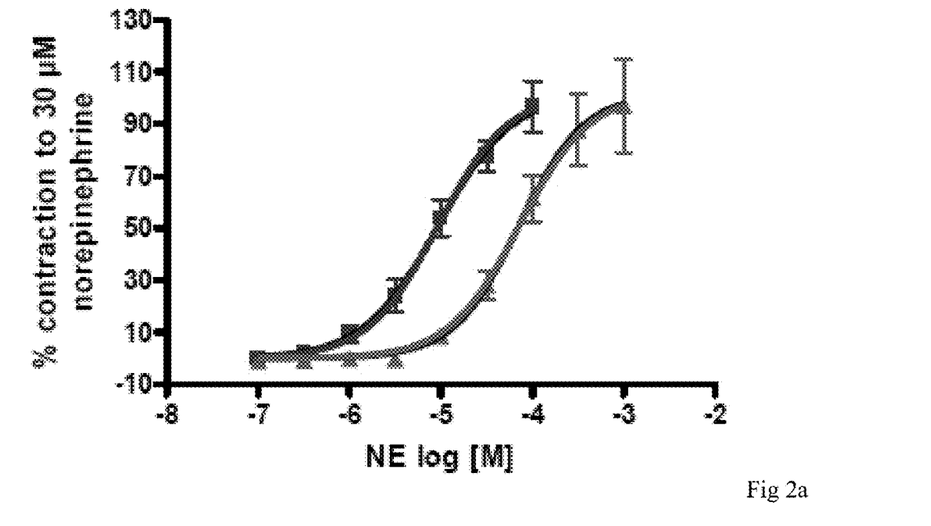
Figure 2B:
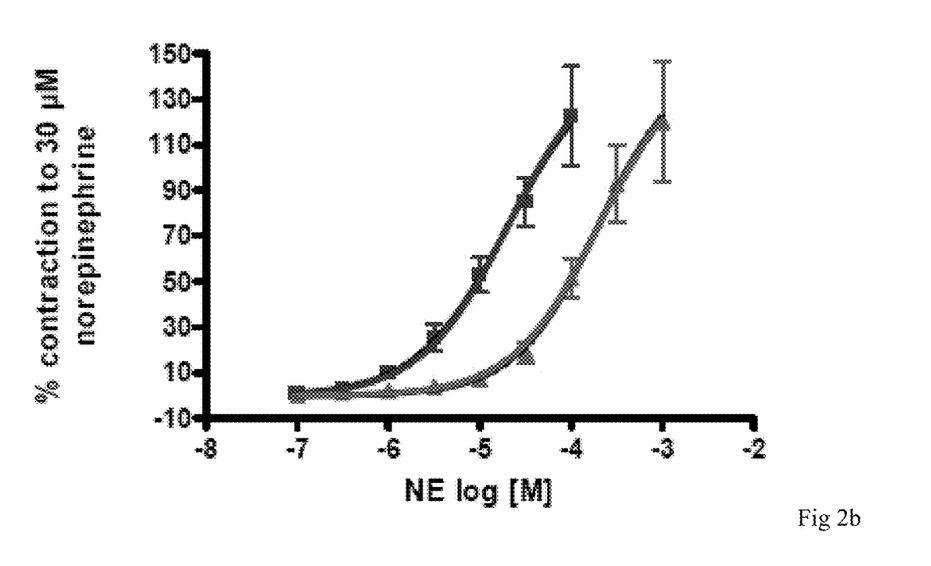
Figure 2C:
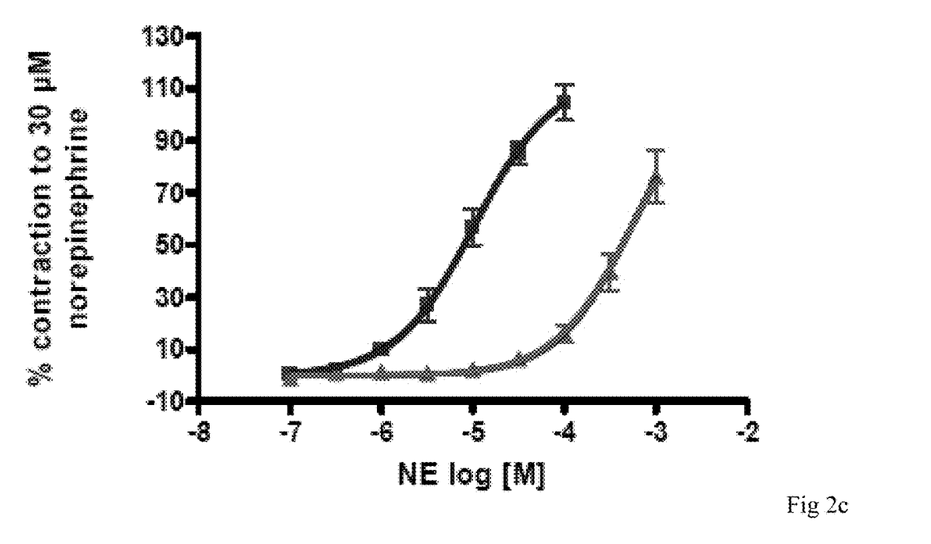

Incubation with 4-[3-[4-(6-fluoro-1,2,-benzisoxazol-3-yl)-1-piperidinyl]propoxy]-3-methoxy-benzoic acid induced concentration-dependent shift in pEC50 of the second CRC to NE, indicating an antagonistic activity, but no effect on Emax values. NE pEC50 values were 4.15+/−0.11 (n=8), 3.69+/−0.24 (n=8), and 3.26+/−0.08 (n=9) in the presence of the test substance at 0.1, 0.3, and 1 uM, respectively. See, FIG. 2.

Dose-ratios obtained were corrected by the dose-ratio obtained in the group treated with the solvent. The $pA_2$ for 4-[3-[4-(6-fluoro-1,2,-benzisoxazol-3-yl)-1-piperidinyl]propoxy]-3-methoxy-benzoic acid, estimated by the Schild Plot was equal to 7.50.

Incubation with 0.01 μM tamsulosin also induced a shift of the second CRC to NE, indicating an antagonistic activity, but no effect on the Emax value. In the presence of tamsulosin, NE pEC50 was 2.96+/−0.20 (n=8).

Following incubation with the solvent (0.1% DMSO) we observed a shift of the second CRC to NE. This result was unexpected since it was previously reported that NE did not induce desensitization of alpha1-adrenoceptors in human isolated prostatic adenoma (Bagot et al., 2005). The only explanation we can advance for this result is an inhibitory effect of 60 min incubation with 0.1% DMSO.

The $pA_2$ of 4-[3-[4-(6-fluoro-1,2,-benzisoxazol-3-yl)-1-piperidinyl]propoxy]-3-methoxy-benzoic acid (7.50) is in accordance with the value previously found on the rabbit isolated prostate. The functional potency of 4-[3-[4-(6-fluoro-1,2,-benzisoxazol-3-yl)-1-piperidinyl]propoxy]-3-methoxy-benzoic acid is also quite similar to pIC50 values obtained in binding studies using the rat alpha1A-adrenoceptor or the cloned human alpha1 D-adrenoceptor (pIC50=7.94 and 7.75, respectively; data communicated by Dr. Baroldi, Vanda Pharmaceuticals). Importantly, it is recognized that blockade of both alpha1A-and alpha1D-adrenoceptors is necessary for optimal clinical effect on BPH patients (Andersson K E, World J. Urol. 19: 390-96, 2002).

The comparison between the antagonistic potencies of 4-[3-[4-(6-fluoro-1,2,-benzisoxazol-3-yl)-1-piperidinyl]propoxy]-3-methoxy-benzoic acid and tamsulosin shows that 4-[3-[4-(6-fluoro-1,2,-benzisoxazol-3-yl)-1-piperidinyl]propoxy]-3-methoxy-benzoic acid is approximately 100 times less potent than tamsulosin on the human alpha1-adrenoceptors expressed in the prostatic adenoma.

This example shows that 4-[3-[4-(6-fluoro-1,2,-benzisoxazol-3-yl)-1-piperidinyl]propoxy]-3-methoxy-benzoic acid is a functional antagonist of the alpha1-adrenoceptors activated by NE on the human adenoma isolated from BPH patients. Its potency is approximately equal to potencies published for some alpha1-adrenoceptor antagonists widely used in US for the treatment of BPH, e.g. alfuzosin, doxazosin, and terazosin.

Example 3

An experiment was conducted to evaluate the effect of 4-[3-[4-(6-fluoro-1,2,-benzisoxazol-3-yl)-1-piperidinyl]propoxy]-3-methoxy-benzoic acid on PE-induced increase in intra-urethal pressure (UP) in anesthetized rats. Briefly, catheters were inserted into the femoral vein of anesthetized male rats for drug administration and into the urethra through the bladder wall for measuring urethral pressure (UP). The test substance, or tamsulosin, was administered 5 minutes before administration of the first dose of PE. The different doses of PE (between 3 and 300 ug/kg in controls and up to 3000 ug/kg in treated animals) were administered intravenously under a volume of 1 mL/kg as a bolus with a 3 minute interval between each dose. Three doses of test substance were used: 10, 33.3 and 100 ug/kg; one dose of tamsulosin: 10 ug/kg; one control group (DMSO 1%).

In the presence of test substance, the dose response curve to PE was dose-dependently shifted to the right. Test substance at 10 ug/kg i.v. showed a statistically significant inhibitory effect on the delta UP (over baseline) induced by 100 ug/kg PE. Test substance at 33.3 ug/kg i.v. showed a statistically significant inhibitory effect on the delta UP (over baseline) induced by 30-100 and 150 ug/kg PE. Test substance at 100 ug/kg i.v., and tamsulosin at 10 ug/kg, produced a statistically significant decrease of the agonist effect in the dose range between 10 and 300 ug/kg.

Therefore, in this study, by intravenous route, 4-[3-[4-(6-fluoro-1,2,-benzisoxazol-3-yl)-1-piperidinyl]propoxy]-3-methoxy-benzoic acid is approximately 10 times less potent than tamsulosin in anesthetized rats. It has been previously shown that alfuzosin (UroXatral®) one of the most prescribed drugs for the treatment of BPH, was 10-fold less potent than tamsulosin (i.v.) in decreasing basal urethral pressure in conscious rats (Martin et al, J. Pharmacol. Exper. Ther. 282: 228-35, 1997).

Example 4

An experiment was conducted to evaluate the antagonistic effect of 4-[3-[4-(6-fluoro-1,2,-benzisoxazol-3-yl)-1-piperidinyl]propoxy]-3-methoxy-benzoic acid on the PE-induced increase in intraurethral pressure (UP) and arterial blood pressure (BP) in anesthetized rats. Oral administration of 4-[3-[4-(6-fluoro-1,2,-benzisoxazol-3-yl)-1-piperidinyl]propoxy]-3-methoxy-benzoic acid or tamsulosin, had no effect on the basal UP measured 25 or 45 minutes later. However, both 4-[3-[4-(6-fluoro-1,2,-benzisoxazol-3-yl)-1-piperidinyl]propoxy]-3-methoxy-benzoic acid and tamsulosin significantly decreased the basal BP levels 25 and 45 minutes after administration.

4-[3-[4-(6-fluoro-1,2,-benzisoxazol-3-yl)-1-piperidinyl]propoxy]-3-methoxy-benzoic acid at 0.5 mg/kg p.o. was ineffective on PE-induced increase of basal UP whereas it had a slight effect at 1.5 and 4.5 mg/kg. Doses of PE increasing baseline UP or BP by 10, 25, 50, 75 and 100% suggest that, for 4-[3-[4-(6-fluoro-1,2,-benzisoxazol-3-yl)-1-piperidinyl]propoxy]-3-methoxy-benzoic acid, the dose of 1.5 m/kg p.o. is more active than one at 4.5 mg/kg. In fact, the UP100% value at 45 min reached the level of statistical significance in the presence of 4-[3-[4-(6-fluoro-1,2,-benzisoxazol-3-yl)-1-piperidinyl]propoxy]-3-methoxy-benzoic acid at 1.5 mg/kg but not at 4.5 mg/kg. At this time, the effect on BP was also significant from BP10% to BP100% in the presence of 4-[3-[4-(6-fluoro-1,2,-benzisoxazol-3-yl)-1-piperidinyl]propoxy]-3-methoxy-benzoic acid at 1.5 mg/kg, whereas no effect was noticed at 4.5 mg/kg.

These results also draw to the conclusion, based on the equipotent effects of 1.5 mg/kg 4-[3-[4-(6-fluoro-1,2,-benzisoxazol-3-yl)-1-piperidinyl]propoxy]-3-methoxy-benzoic acid at 45 min post-administration and 0.3 mg/kg tamsulosin, that 4-[3-[4-(6-fluoro-1,2,-benzisoxazol-3-yl)-1-piperidinyl]propoxy]-3-methoxy-benzoic acid is about 5 times less potent than tamsulosin by oral route, on both UP and BP.

For comparison, silodosin administered intraduodenally was 2.8 times less potent than tamsulosin on UP in a similar experimental model on rats (Akiyama et al., Pharmacol. Exp. Ther. 291: 81-91, 1999).

In another experiment, the effect of a 1-week treatment with 4-[3-[4-(6-fluoro-1,2,-benzisoxazol-3-yl)-1-piperidinyl]propoxy]-3-methoxy-benzoic acid, tamulosin, and a common vehicle on bladder outlet obstruction-induced bladder dysfunction in rats was evaluated. Although tamsulosin is reported to have been shown to be positive in the model employed, in this experiment, tamsulosin was completely ineffective on cystometric parameters. 4-[3-[4-(6-fluoro-1,2,-benzisoxazol-3-yl)-1-piperidinyl]propoxy]-3-methoxy-benzoic acid was also devoid of significant effect on all cystometric parameters but significantly decreased the amplitude of unstable contractions. However, this latter effect was exclusively observed at the lowest dose tested (1 mg/kg/day). Tamsulosin and 4-[3-[4-(6-fluoro-1,2,-benzisoxazol-3-yl)-1-piperidinyl]propoxy]-3-methoxy-benzoic acid were both devoid of effect on the bladder hypertrophy secondary to outlet obstruction.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:

1. A method for treating hypertension in an individual in need of such treatment, the method comprising antagonizing an alpha adrenoceptor in the individual by administering to the individual an effective amount of 4-[3-[4-(6-fluoro-1,2,-benzisoxazol-3-yl)-1-piperidinyl]propoxy]-3-methoxy-benzoic acid or a pharmaceutically acceptable salt thereof.

2. The method of claim 1, wherein the individual is human.

3. The method of claim 1, wherein the individual is also treated with one or more additional alpha adrenoceptor antagonists.

4. The method of claim 3, wherein the one or more additional alpha adrenoceptor antagonists are selected from a group consisting of: doxazosin, prazosin, terazosin, Rec 15/2739, and tamsulosin.

5. The method of claim 1, wherein the individual is also treated with a second agent selected from a group consisting of: one or more additional alpha adrenoceptor antagonists, one or more steroid-5-alpha reductase inhibitors, and one or more additional alpha adrenoceptor antagonists in combination with one or more steroid-5-alpha reductase inhibitors.

6. The method of claim 1, wherein the individual is also treated with finasteride.

7. The method of claim 1, wherein the 4-[3-[4-(6-fluoro-1,2,-benzisoxazol-3-yl)-1-piperidinyl]propoxy]-3-methoxy-benzoic acid or pharmaceutically acceptable salt thereof administered to the individual is about 1 to about 500 mg/day.

8. The method of claim 7, wherein the amount of 4-[3-[4-(6-fluoro-1,2,-benzisoxazol-3-yl)-1-piperidinyl]propoxy]-3-methoxy-benzoic acid or pharmaceutically acceptable salt thereof administered to the individual is about 5 to about 100 mg/day.

9. The method of claim 7, wherein the amount of 4-[3-[4-(6-fluoro-1,2,-benzisoxazol-3-yl)-1-piperidinyl]propoxy]-3-methoxy-benzoic acid or pharmaceutically acceptable salt thereof administered to the individual is about 0.01 to about 10 mg/kg/day.

10. The method of claim 7, wherein the amount of 4-[3-[4-(6-fluoro-1,2,-benzisoxazol-3-yl)-1-piperidinyl]propoxy]-3-methoxy-benzoic acid or pharmaceutically acceptable salt thereof administered to the individual is 0.5 to 1.5 mg/kg/day.

11. A pharmaceutical composition that comprises 4-[3-[4-(6-fluoro-1,2,-benzisoxazol-3-yl)-1-piperidinyl]propoxy]-3-methoxy-benzoic acid or a pharmaceutically acceptable salt thereof, in one or more dosage units, for the treatment of hypertension; and a pharmaceutically acceptable excipient.

12. The pharmaceutical composition of claim 11 that is a controlled release formulation.

13. The pharmaceutical composition of claim 11, further comprising at least one additional alpha adrenoceptor antagonist selected from a group consisting of: doxazosin, prazosin, terazosin, Rec 15/2739, and tamsulosin.

* * * * *